United States Patent
Peyser

(10) Patent No.: US 12,138,427 B2
(45) Date of Patent: Nov. 12, 2024

(54) TIME AVERAGED BASAL RATE OPTIMIZER

(71) Applicant: DexCom, Inc., San Diego, CA (US)

(72) Inventor: Thomas A. Peyser, Menlo Park, CA (US)

(73) Assignee: Dexcom, Inc., San Diego, CA (US)

( * ) Notice: Subject to any disclaimer, the term of this patent is extended or adjusted under 35 U.S.C. 154(b) by 0 days.

(21) Appl. No.: 18/653,050

(22) Filed: May 2, 2024

(65) Prior Publication Data

US 2024/0277935 A1 Aug. 22, 2024

Related U.S. Application Data

(63) Continuation of application No. 18/433,530, filed on Feb. 6, 2024, which is a continuation of application (Continued)

(51) Int. Cl.
*A61M 5/172* (2006.01)
*A61B 5/145* (2006.01)
(Continued)

(52) U.S. Cl.
CPC ....... *A61M 5/1723* (2013.01); *A61B 5/14532* (2013.01); *G16H 20/17* (2018.01); *G16H 40/67* (2018.01); *G16Z 99/00* (2019.02); *A61M 2005/1726* (2013.01); *A61M 2202/0007* (2013.01); *A61M 2202/07* (2013.01); *A61M 2205/3303* (2013.01);
(Continued)

(58) Field of Classification Search
CPC ...... A61B 5/14532; A61M 2005/1726; A61M 2202/0007; A61M 2202/07; A61M 2205/3303; A61M 2205/3306; A61M 2205/3313; A61M 2205/3584; A61M 2205/3592; A61M 2205/50; A61M 5/1723; G06F 19/3468
See application file for complete search history.

(56) References Cited

U.S. PATENT DOCUMENTS 4,703,756 A 11/1987 Gough et al.
5,019,974 A 5/1991 Beckers
(Continued)

FOREIGN PATENT DOCUMENTS

EP 1338295 A1 8/2003
WO 03022327 A2 3/2003
(Continued)

OTHER PUBLICATIONS

American Diabetes Association., "Position Statement: Diagnosis and Classification of Diabetes Mellitus," Diabetes Care, vol. 30, Supplement 01, Jan. 2007, pp. S42-S47.
(Continued)

*Primary Examiner* — Jason E Flick
(74) *Attorney, Agent, or Firm* — Stuart H. Mayer; Kaplan Breyer Schwarz LLP

(57) ABSTRACT

Systems and methods for integrating a continuous glucose sensor, including a receiver, a medicament delivery device, a controller module, and optionally a single point glucose monitor are provided. Integration may be manual, semi-automated and/or fully automated.

30 Claims, 2 Drawing Sheets

Related U.S. Application Data

No. 18/367,164, filed on Sep. 12, 2023, now Pat. No. 11,957,877, which is a continuation of application No. 17/039,751, filed on Sep. 30, 2020, now Pat. No. 11,813,433, which is a continuation of application No. 16/144,782, filed on Sep. 27, 2018, now Pat. No. 10,821,229, which is a continuation of application No. 14/307,219, filed on Jun. 17, 2014, now Pat. No. 10,112,011.

(60) Provisional application No. 61/856,537, filed on Jul. 19, 2013.

(51) Int. Cl.
G16H 20/17 (2018.01)
G16H 40/67 (2018.01)
G16Z 99/00 (2019.01)

(52) U.S. Cl.
CPC .............. A61M 2205/3306 (2013.01); A61M 2205/3313 (2013.01); A61M 2205/3584 (2013.01); A61M 2205/3592 (2013.01); A61M 2205/50 (2013.01)

(56) References Cited

U.S. PATENT DOCUMENTS

| | | | |
|---|---|---|---|
| 5,101,814 A | 4/1992 | Palti | |
| 5,429,602 A | 7/1995 | Hauser | |
| 5,474,552 A | 12/1995 | Palti | |
| 5,569,186 A | 10/1996 | Lord et al. | |
| 5,660,565 A | 8/1997 | Williams | |
| 5,665,065 A | 9/1997 | Colman et al. | |
| 5,674,289 A | 10/1997 | Fournier et al. | |
| 5,733,259 A | 3/1998 | Valcke et al. | |
| 5,919,216 A | 7/1999 | Houben et al. | |
| 5,925,021 A | 7/1999 | Castellano et al. | |
| 6,135,978 A | 10/2000 | Houben et al. | |
| 6,163,720 A | 12/2000 | Gyory et al. | |
| 6,175,752 B1 | 1/2001 | Say et al. | |
| 6,234,964 B1 | 5/2001 | Iliff | |
| 6,248,067 B1 | 6/2001 | Causey, III et al. | |
| 6,302,855 B1 | 10/2001 | Lav et al. | |
| 6,312,388 B1 | 11/2001 | Marcovecchio et al. | |
| 6,424,847 B1 | 7/2002 | Mastrototaro et al. | |
| 6,477,395 B2 | 11/2002 | Schulman et al. | |
| 6,512,939 B1 | 1/2003 | Colvin et al. | |
| 6,544,212 B2 | 4/2003 | Galley et al. | |
| 6,549,796 B2 | 4/2003 | Sohrab | |
| 6,557,899 B2 | 5/2003 | Martin-Cocher et al. | |
| 6,558,320 B1 | 5/2003 | Causey, III et al. | |
| 6,558,351 B1 | 5/2003 | Steil et al. | |
| 6,558,955 B1 | 5/2003 | Kristal et al. | |
| 6,562,001 B2 | 5/2003 | Lebel et al. | |
| 6,565,509 B1 | 5/2003 | Say et al. | |
| 6,571,128 B2 | 5/2003 | Lebel et al. | |
| 6,572,545 B2 | 6/2003 | Knobbe et al. | |
| 6,577,899 B2 | 6/2003 | Lebel et al. | |
| 6,620,138 B1 | 9/2003 | Marrgi et al. | |
| 6,635,014 B2 | 10/2003 | Starkweather et al. | |
| 6,648,821 B2 | 11/2003 | Lebel et al. | |
| 6,740,072 B2 | 5/2004 | Starkweather et al. | |
| 6,750,055 B1 | 6/2004 | Connelly et al. | |
| 6,832,200 B2 | 12/2004 | Greeven et al. | |
| 6,875,195 B2 | 4/2005 | Choi | |
| 6,936,029 B2 | 8/2005 | Mann et al. | |
| 7,025,743 B2 | 4/2006 | Mann et al. | |
| 7,044,911 B2 | 5/2006 | Drinan et al. | |
| 7,060,059 B2 | 6/2006 | Keith et al. | |
| 7,267,665 B2 | 9/2007 | Steil et al. | |
| 7,278,983 B2 | 10/2007 | Ireland et al. | |
| 7,282,029 B1 | 10/2007 | Poulsen et al. | |
| 7,344,500 B2 | 3/2008 | Talbot et al. | |
| 7,519,408 B2 | 4/2009 | Rasdal et al. | |
| 7,569,030 B2 | 8/2009 | Lebel et al. | |
| 7,591,801 B2 | 9/2009 | Brauker et al. | |
| 7,647,237 B2 | 1/2010 | Malave et al. | |
| 7,670,288 B2 | 3/2010 | Sher | |
| 7,901,394 B2 | 3/2011 | Ireland et al. | |
| 7,946,985 B2 | 5/2011 | Mastrototaro et al. | |
| 8,512,276 B2 | 8/2013 | Talbot et al. | |
| 8,808,228 B2 | 8/2014 | Brister et al. | |
| 10,112,011 B2 | 10/2018 | Peyser | |
| 2001/0007950 A1 | 7/2001 | North et al. | |
| 2002/0045808 A1 | 4/2002 | Ford et al. | |
| 2002/0065453 A1 | 5/2002 | Lesho et al. | |
| 2003/0028089 A1 | 2/2003 | Galley et al. | |
| 2003/0060692 A1 | 3/2003 | L. Ruchti et al. | |
| 2003/0060753 A1 | 3/2003 | Starkweather et al. | |
| 2003/0114836 A1 | 6/2003 | Estes et al. | |
| 2003/0187338 A1 | 10/2003 | Say et al. | |
| 2003/0208113 A1 | 11/2003 | Mault et al. | |
| 2004/0044272 A1 | 3/2004 | Moerman et al. | |
| 2004/0068230 A1 | 4/2004 | Estes et al. | |
| 2004/0122297 A1 | 6/2004 | Stahmann et al. | |
| 2004/0122353 A1 | 6/2004 | Shahmirian et al. | |
| 2004/0162678 A1 | 8/2004 | Hetzel et al. | |
| 2005/0027462 A1 | 2/2005 | Goode et al. | |
| 2005/0113653 A1 | 5/2005 | Fox et al. | |
| 2005/0113744 A1 | 5/2005 | Donoghue et al. | |
| 2005/0203360 A1 | 9/2005 | Brauker et al. | |
| 2005/0245904 A1 | 11/2005 | Estes et al. | |
| 2006/0173406 A1 | 8/2006 | Hayes et al. | |
| 2007/0032706 A1 | 2/2007 | Kamath et al. | |
| 2007/0066956 A1 | 3/2007 | Finkel | |
| 2007/0100222 A1 | 5/2007 | Mastrototaro et al. | |
| 2007/0106135 A1 | 5/2007 | Sloan et al. | |
| 2007/0112298 A1 | 5/2007 | Mueller, Jr. et al. | |
| 2007/0173761 A1 | 7/2007 | Kanderian, Jr. et al. | |
| 2007/0179434 A1 | 8/2007 | Weinert et al. | |
| 2007/0293742 A1 | 12/2007 | Simonsen et al. | |
| 2008/0097289 A1 | 4/2008 | Steil et al. | |
| 2008/0269723 A1 | 10/2008 | Mastrototaro et al. | |
| 2009/0177147 A1* | 7/2009 | Blomquist ..........A61M 5/1723 702/19 | |
| 2010/0332142 A1 | 12/2010 | Shadforth et al. | |
| 2011/0021898 A1 | 1/2011 | Wei et al. | |
| 2012/0097289 A1 | 4/2012 | Chun et al. | |
| 2012/0226259 A1* | 9/2012 | Yodfat ....................G16H 40/63 604/500 | |
| 2012/0227737 A1 | 9/2012 | Mastrototaro et al. | |
| 2012/0259278 A1 | 10/2012 | Hayes et al. | |

FOREIGN PATENT DOCUMENTS

| | | |
|---|---|---|
| WO | 2004009161 A1 | 1/2004 |
| WO | 2006021430 A2 | 3/2006 |
| WO | 2009023406 A1 | 2/2009 |
| WO | 2011030343 A1 | 3/2011 |

OTHER PUBLICATIONS

American Diabetes Association., "Position Statement: Standards of Medical Care in Diabetes," Diabetes Care, vol. 30, Supplement 01, Jan. 2007, pp. S4-S41.

American Diabetes Association., "Summary of Revisions for the 2007 Clinical Practice Recommendations," Diabetes Care, vol. 30, Supplement 01, Jan. 2007, pp. S3.

Aussedat B., et al., "Interstitial Glucose Concentration and Glycemia: Implications for Continuous Subcutaneous Glucose Monitoring," American Journal of Physiology—Endocrinology and Metabolism, vol. 278 (4), Apr. 1, 2000, pp. E716-E728.

Chase J.G., et al., "Targeted Glycemic Reduction in Critical Care Using Closed-Loop Control," Diabetes Technology Therapeutics, vol. 7 (2), 2005, pp. 274-282.

Cobelli C., etal., "Artificial Pancreas: Past, Present Future," Diabetes, vol. 60(11), Nov. 2011, pp. 2672-2682.

El-Khatib F.H., et al., "Adaptive Closed-Loop Control Provides Blood-Glucose Regulation Using Dual Subcutaneous Insulin and Glucagon Infusion in Diabetic Swine," Journal of Diabetes Science

(56) References Cited

OTHER PUBLICATIONS and Technology, Diabetes Technology Society, vol. 1 (2), 2007, pp. 181-192.
Elleri D., et al., "Closed Loop Basal Insulin Delivery Over 36 Hours in Adolescents With Type 1 Diabetes," Diabetes Care, vol. 36, Apr. 2013, pp. 838-844.
Frohnauer M.K., et al., "Graphical Human Insulin Time-Activity Profiles Using Standardized Definitions," Diabetes Technology & Therapeutics, vol. 3 (3), 2001, pp. 419-429.
Garg S.K., et al., "Improved Glucose Excursions Using an Implantable Real-Time Continuous Glucose Sensor in Adults With Type 1 Diabetes," Emerging Treatments and Technologies, Diabetes Care, vol. 27 (3), 2004, pp. 734-738.
Garg S.K., "New Insulin Analogues," Diabetes Technology & Therapeutics, vol. 7 (5), 2005, pp. 813-817.
Hagvik J., "Glucose Measurement: Time for a Gold Standard," Journal of Diabetes Science and Technology, vol. 1 (2), Mar. 2007, pp. 169-172.
Heinemann L., et al., "Review: Measurement of Insulin Absorption and Insulin Action," Diabetes Technology & Therapeutics, vol. 6 (5), 2004, pp. 698-718.
Heinemann L., "Measurement Quality of Blood Glucose Meters: Is There a Need for an Institution with an Unbiased View?," Journal of Diabetes Science and Technology, vol. 1 (2), Mar. 2007, pp. 178-180.
Heinemann L., "Review: Variability of Insulin Absorption and Insulin Action," Diabetes Technology & Therapeutics, vol. 4 (5), 2002, pp. 673-682.
Hovorka R., et al., "Closing the Loop: The Adicol Experience," Diabetes Technology & Therapeutics, vol. 6 (3), 2004, pp. 307-318.
Hunsley B., et al.. "Whole Blood Glucose Standard Is Key to Accurate Insulin Dosages," Journal of Diabetes Science and Technology, vol. 1 (2), Mar. 2007, pp. 173-177.
International Preliminary Report on Patentability for Application No. PCT/US2014/042741 mailed Jan. 28, 2016, 9 pages.
International Search Report and Written Opinion for Application No. PCT/US2014/042741 mailed Dec. 11, 2014, 11 pages.
Jones S.M., et al., "Optimal Insulin Pump Dosing and Postprandial Glycemia Following a Pizza Meal Using the Continuous Glucose Monitoring System," Diabetes Technology Therapeutics, vol. 7 (2), Apr. 2005, pp. 233-240.
Kizilel S., et al., "Review: The Bioartificial Pancreas: Progress and Challenges," Diabetes Technology & Therapeutics, vol. 7 (6), 2005, pp. 968-985.

Klonoff D.C., "Editorial: Current, Emerging, and Future Trends in Metabolic Monitoring," Diabetes Technology & Therapeutics, vol. 4 (5), 2002, pp. 583-588.
Koschinsky T., et al., "Review: Glucose Sensors and the Alternate Site Testing-like Phenomenon: Relationship Between Rapid Blood Glucose Changes and Glucose Sensor Signals," Diabetes Technology & Therapeutics, vol. 5 (5), 2003, pp. 829-842.
Lee S.W., et al., "Combined Insulin Pump Therapy with Real-Time Continuous Glucose Monitoring Significantly Improves Glycemic Control Compared to Multiple Daily Injection Therapy in Pump Naïve Patients with Type 1 Diabetes; Single Center Pilot Study Experience," Journal of Diabetes Science and Technology, vol. 1 (3), May 2007, pp. 400-404.
Marling et al., "Characterizing Blood Glucose Variability Using New Metrics with Continuous Glucose Monitoring", Journal of Diabetes Science & Technology, vol. 5(4), Jul. 2011, 871-878.
Medtronic Minimed, Paradigm 512 and 712 Infusion Pumps Guide, User Guide, 2005, 149 pages.
NewsRx, "Glucose Monitoring: FDA OKs New Device to Manage Diabetes," Medical Letter on the CDC & FDA via NewsRx. com, Aug. 3, 2003, 1 page.
Palerm et al., "A Run-to-Run Control Strategy to Adjust Basal Insulin Infusion Rates in Type 1 Diabetes", J. Process Control, 2008, vol. 18(3-4), pp. 258-265.
Renard E., "Implantable Closed-Loop Glucose Sensing and Insulin Delivery: The Future for Insulin Pump Therapy," Current Opinion in Pharmacology, vol. 2 (6), 2002, pp. 708-716.
Ristic S., et al., "Review: Effects of Rapid-Acting Insulin Analogs on Overall Glycemic Control in Type 1 and Type 2 Diabetes Mellitus," Diabetes Technology & Therapeutics, vol. 5 (1), 2003, pp. 57-66.
Thennadil S.N., et al., "Comparison of Glucose Concentration in Interstitial Fluid, and Capillary and Venous Blood During Rapid Changes in Blood Glucose Levels," Diabetes Technology & Therapeutics, vol. 3 (3), 2001, pp. 357-365.
Vesper H.W., et al., "Assessment of Trueness of a Glucose Monitor Using Interstitial Fluid and Whole Blood as Specimen Matrix," Diabetes Technology & Therapeutics, vol. 8 (1), 2006, pp. 76-80.
Wentholt I.M.E., et al., "Relationship between Interstitial and Blood Glucose in Type 1 Diabetes Patients: Delay and the Push-pull Phenomenon Revisited," Diabetes Technology & Therapeutics, vol. 9 (2), 2007, pp. 169-175.
Wolpert H.A., "Commentary: A Clinician's Perspective on Some of the Challenges in Closed Loop," Diabetes Technology & Therapeutics, vol. 5 (5), 2003, pp. 843-846.

* cited by examiner

TIME AVERAGED BASAL RATE OPTIMIZER

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of Ser. No. 18/433,530, filed Feb. 6, 2024, which is a continuation of U.S. Ser. No. 18/367,164 filed Sep. 12, 2023, which is a continuation of U.S. application Ser. No. 17/039,751, filed Sep. 30, 2020, which is a continuation U.S. application Ser. No. 16/144,782, filed Sep. 27, 2018, which is a continuation of U.S. application Ser. No. 14/307,219, filed Jun. 17, 2014, now U.S. Pat. No. 10,112,011, which claims the benefit of U.S. Provisional Application No. 61/856,537, filed Jul. 19, 2013. Each of the aforementioned applications is incorporated by reference herein in its entirety, and each is hereby expressly made a part of this specification.

FIELD OF THE INVENTION

An integrated medicament delivery device and continuous glucose sensor, including systems and methods for processing sensor and insulin data, are provided.

BACKGROUND

Diabetes mellitus is a disorder in which the pancreas cannot create sufficient insulin (Type I or insulin dependent) and/or in which insulin is not effective (Type 2 or non-insulin dependent). In the diabetic state, the victim suffers from high glucose, which may cause an array of physiological derangements (for example, kidney failure, skin ulcers, or bleeding into the vitreous of the eye) associated with the deterioration of small blood vessels. A hypoglycemic reaction (low glucose) may be induced by an inadvertent overdose of insulin, or after a normal dose of insulin or glucose-lowering agent accompanied by extraordinary exercise or insufficient food intake.

Current approaches to open, semi-closed and/or closed loop therapy for diabetes rely on real-time insulin dosing instructions to replace pre-programmed basal rate infusion in standard insulin pump or continuous subcutaneous insulin infusion (CSII) therapy. These systems generally combine real-time continuous glucose monitoring with control algorithms to modulate insulin infusion so as to maintain the patients' blood glucose within a specified euglycemic target range.

One of the most significant problems with current open-loop CSII therapy is the difficulty encountered by patients in establishing the correct pattern of basal rates over the course of an entire day. In addition, basal rates that are appropriate to maintain euglycemia on one day with a high level of physical activity may be inadequate on another day with a lower level of physical activity and vice versa. Similarly, basal rates set on one day with a concurrent illness may be inappropriate for another day with the patient in otherwise good health.

SUMMARY

Time averaging of optimized basal rates is a method for initializing the real-time basal rate optimization with the best possible starting basal rate profile.

In a first aspect, a method for optimizing a basal rate profile for use with continuous insulin therapy is provided. The method comprises providing a programmed basal rate profile for insulin therapy, wherein the basal rate profile comprises an insulin delivery schedule that includes one or more blocks of time, and wherein each block defines an insulin delivery rate; periodically or intermittently updating the programmed basal rate profile based on a retrospective analysis of continuous glucose sensor data over a predetermined time window; and optionally adjusting the basal rate profile of the updated programmed basal rate profile in response to real time continuous glucose sensor data indicative of actual or impending hyperglycemia or hypoglycemia.

In a generally applicable embodiment (i.e. independently combinable with any of the aspects or embodiments identified herein) of the first aspect, the pre-programmed basal rate profile is programmed by a patient or healthcare provider.

In a generally applicable embodiment (i.e. independently combinable with any of the aspects or embodiments identified herein) of the first aspect, the basal rate profile is selected by a user from a list of predetermined basal rate profiles.

In a generally applicable embodiment (i.e. independently combinable with any of the aspects or embodiments identified herein) of the first aspect, the method further comprises iteratively repeating the providing and updating, wherein the programmed basal rate profile is an updated basal rate profile from a previous iteration. In some embodiments, the previous iteration is from about one day to one week previous to the iteration.

In a generally applicable embodiment (i.e. independently combinable with any of the aspects or embodiments identified herein) of the first aspect, the basal rate profile consists of a single rate of insulin infusion over 24 hours.

In a generally applicable embodiment (i.e. independently combinable with any of the aspects or embodiments identified herein) of the first aspect, the basal rate profile comprises a plurality of rates associated with different time blocks spanning 24 hours.

In a generally applicable embodiment (i.e. independently combinable with any of the aspects or embodiments identified herein) of the first aspect, the retrospective analysis comprises a time-averaging of the continuous glucose sensor data.

In a generally applicable embodiment (i.e. independently combinable with any of the aspects or embodiments identified herein) of the first aspect, the periodically or intermittently updating the programmed basal rate profile is further based on a retrospective analysis of insulin data over a predetermined time window. In some embodiments, the retrospective analysis comprises a time-averaging of the insulin data.

In a generally applicable embodiment (i.e. independently combinable with any of the aspects or embodiments identified herein) of the first aspect, the predetermined time window is about 3 to 7 days.

In a generally applicable embodiment (i.e. independently combinable with any of the aspects or embodiments identified herein) of the first aspect, the periodically or intermittently updating is performed once a day.

In a generally applicable embodiment (i.e. independently combinable with any of the aspects or embodiments identified herein) of the first aspect, the periodically or intermittently updating is triggered by an event.

In a generally applicable embodiment (i.e. independently combinable with any of the aspects or embodiments identified herein) of the first aspect, the periodically or intermittently updating is triggered based on a recognized pattern in the data. In some embodiments, the recognized pattern comprises a measure of glycemic variability.

In a generally applicable embodiment (i.e. independently combinable with any of the aspects or embodiments identified herein) of the first aspect, the updated basal rate profile more closely correlates the patients' daily insulin dosing requirements as compared to the programmed basal rate profile.

In a generally applicable embodiment (i.e. independently combinable with any of the aspects or embodiments identified herein) of the first aspect, optionally adjusting comprises dynamically increasing or decreasing the basal rate of the updated programmed basal rate profile in real time in response to real time continuous glucose sensor data indicating actual or impending hyperglycemia or hypoglycemia In a generally applicable embodiment (i.e. independently combinable with any of the aspects or embodiments identified herein) of the first aspect, periodically or intermittently updating the basal rate profile comprises providing upper or lower limits insulin delivery.

In a generally applicable embodiment (i.e. independently combinable with any of the aspects or embodiments identified herein) of the first aspect, optionally adjusting comprises controlling insulin delivery within the upper and lower limits.

In a second aspect, an integrated system for monitoring a glucose concentration in a host and for delivering insulin to a host, the system is provided. The system comprises a continuous glucose sensor, wherein the continuous glucose sensor is configured to substantially continuously measure a glucose concentration in a host, and to provide continuous sensor data associated with the glucose concentration in the host; an insulin delivery device configured to deliver insulin to the host, wherein the insulin delivery device is operably connected to the continuous glucose sensor; and a processor module configured to perform any one of the embodiments of the first aspect.

Any of the features of an embodiment of the first or second aspects is applicable to all aspects and embodiments identified herein. Moreover, any of the features of an embodiment of the first or second aspects is independently combinable, partly or wholly with other embodiments described herein in any way, e.g., one, two, or three or more embodiments may be combinable in whole or in part. Further, any of the features of an embodiment of the first or second aspects may be made optional to other aspects or embodiments. Any aspect or embodiment of a method can be performed by a system or apparatus of another aspect or embodiment, and any aspect or embodiment of a system can be configured to perform a method of another aspect or embodiment.

DETAILED DESCRIPTION OF EXEMPLARY EMBODIMENTS

Figure 1:
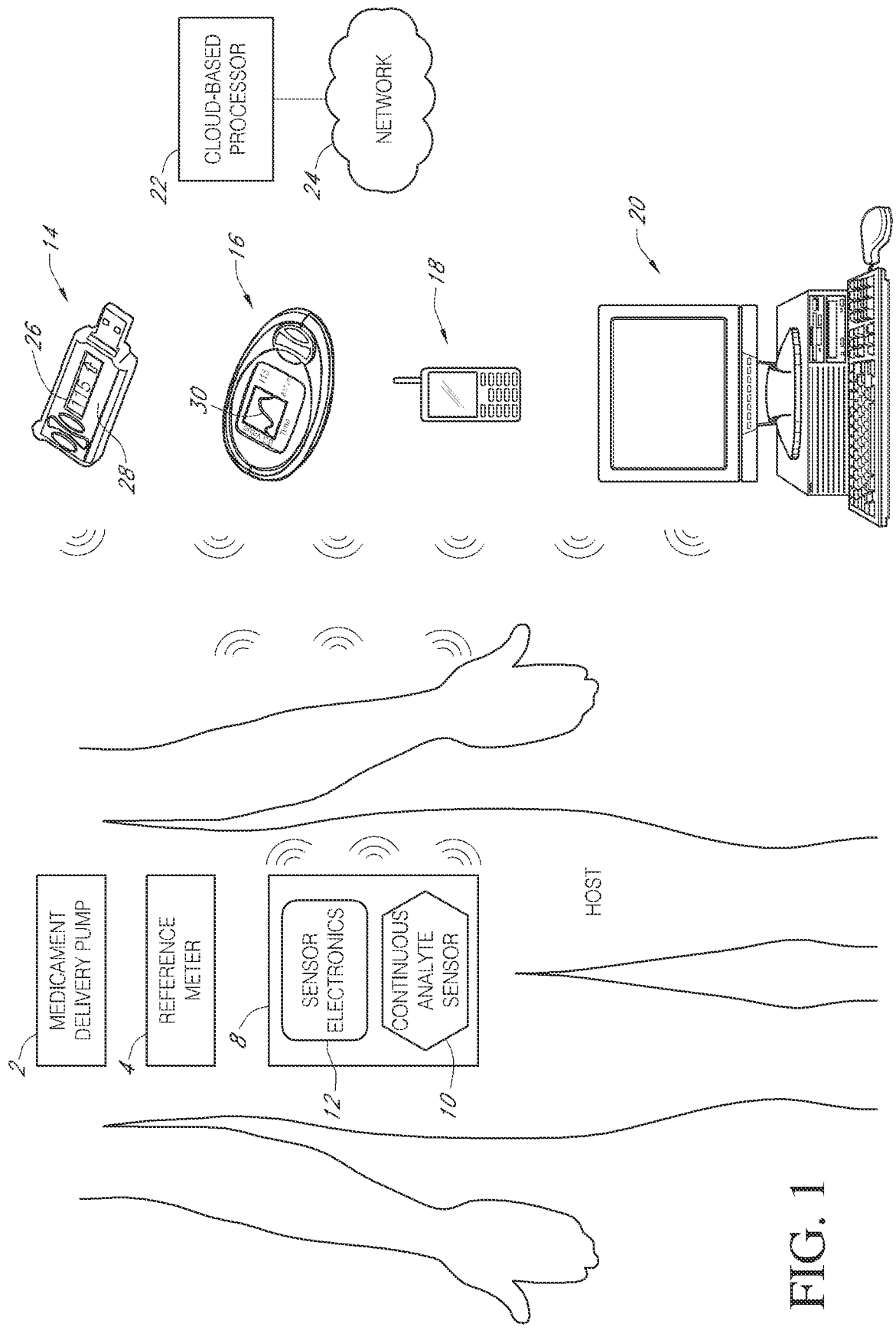
FIG. 1 is a block diagram of an integrated system of the preferred embodiments, including a continuous glucose sensor and a medicament delivery device.

The following description and examples illustrate some exemplary embodiments of the disclosed invention in detail.

Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "continuous glucose sensor," as used herein is a broad term, and is to be given its ordinary and customary meaning to a person of ordinary skill in the art (and is not to be limited to a special or customized meaning), and refers without limitation to a device that continuously or continually measures the glucose concentration of a bodily fluid (e.g., blood, plasma, interstitial fluid and the like), for example, at time intervals ranging from fractions of a second up to, for example, 1, 2, or 5 minutes, or longer. It should be understood that continual or continuous glucose sensors can continually measure glucose concentration without requiring user initiation and/or interaction for each measurement, such as described with reference to U.S. Pat. No. 6,001,067, for example.

The phrase "continuous glucose sensing," as used herein is a broad term, and is to be given its ordinary and customary meaning to a person of ordinary skill in the art (and is not to be limited to a special or customized meaning), and refers without limitation to the period in which monitoring of the glucose concentration of a host's bodily fluid (e.g., blood, serum, plasma, extracellular fluid, etc.) is continuously or continually performed, for example, at time intervals ranging from fractions of a second up to, for example, 1, 2, or 5 minutes, or longer. In one exemplary embodiment, the glucose concentration of a host's extracellular fluid is measured every 1, 2, 5, 10, 20, 30, 40, 50 or 60-seconds.

The term "substantially" as used herein is a broad term, and is to be given its ordinary and customary meaning to a person of ordinary skill in the art (and is not to be limited to a special or customized meaning), and refers without limitation to being largely but not necessarily wholly that which is specified, which may include an amount greater than 50 percent, an amount greater than 60 percent, an amount greater than 70 percent, an amount greater than 80 percent, an amount greater than 90 percent or more.

The terms "processor" and "processor module," as used herein are a broad terms, and are to be given their ordinary and customary meaning to a person of ordinary skill in the art (and are not to be limited to a special or customized meaning), and refer without limitation to a computer system, state machine, processor, or the like designed to perform arithmetic or logic operations using logic circuitry that responds to and processes the basic instructions that drive a computer. In some embodiments, the terms can include ROM and/or RAM associated therewith.

The term "basal," as used herein is a broad term, and is to be given its ordinary and customary meaning to a person of ordinary skill in the art (and is not to be limited to a special or customized meaning), and refers without limitation to the minimum required rate or other value for something to function. For example, in the case of insulin therapy, the term "basal rate" can refer to a regular (e.g., in accordance with fixed order or procedure, such as regularly scheduled for/at a fixed time), periodic or continuous delivery of low levels of insulin, such as but not limited to throughout a 24-hour period.

The term "basal rate profile," as used herein is a broad term, and is to be given its ordinary and customary meaning to a person of ordinary skill in the art (and is not to be limited to a special or customized meaning), and refers without limitation to an insulin delivery schedule that includes one or more blocks of time (e.g., time blocks), wherein each block defines an insulin delivery rate.

Exemplary embodiments disclosed herein relate to the use of a glucose sensor that measures a concentration of glucose or a substance indicative of the concentration or presence of the analyte. In some embodiments, the glucose sensor is a continuous device, for example a subcutaneous, transdermal, transcutaneous, and/or intravascular (e.g., intravenous) device. In some embodiments, the device can analyze a plurality of intermittent blood samples. The glucose sensor can use any method of glucose-measurement, including enzymatic, chemical, physical, electrochemical, optical, optochemical, fluorescence-based, spectrophotometric, spectroscopic (e.g., optical absorption spectroscopy, Raman spectroscopy, etc.), polarimetric, calorimetric, iontophoretic, radiometric, and the like.

The glucose sensor can use any known detection method, including invasive, minimally invasive, and non-invasive sensing techniques, to provide a data stream indicative of the concentration of the analyte in a host. The data stream is typically a raw data signal that is used to provide a useful value of the analyte to a user, such as a patient or health care professional (e.g., doctor), who may be using the sensor.

Although much of the description and examples are drawn to a glucose sensor, the systems and methods of embodiments can be applied to any measurable analyte. In some embodiments, the analyte sensor is a glucose sensor capable of measuring the concentration of glucose in a host. Some exemplary embodiments described below utilize an implantable glucose sensor. However, it should be understood that the devices and methods described herein can be applied to any device capable of detecting a concentration of analyte and providing an output signal that represents the concentration of the analyte.

In some embodiments, the analyte sensor is an implantable glucose sensor, such as described with reference to U.S. Pat. No. 6,001,067 and U.S. Patent Publication No. US-2011-0027127-A1. In some embodiments, the analyte sensor is a transcutaneous glucose sensor, such as described with reference to U.S. Patent Publication No. US-2006-0020187-A1. In yet other embodiments, the analyte sensor is a dual electrode analyte sensor, such as described with reference to U.S. Patent Publication No. US-2009-0137887-A1. In still other embodiments, the sensor is configured to be implanted in a host vessel or extracorporeally, such as is described in U.S. Patent Publication No. US-2007-0027385-A1. The patents and publications are incorporated herein by reference in their entirety.

In order to improve diabetes management, therapy in an open, semi-closed and/or closed loop therapy can be provided that performs a periodic optimization of the pre-programmed basal rate profile alone based on input from a continuous glucose monitor. The optimized basal rate profile can increase the effectiveness of a real-time basal rate adjustment because the basal rate profile is optimized to correlate to the patients' unique and changing daily insulin requirements. Real time basal rate optimization within specified upper and lower limits can provide patients with improved glycemic control with a minimum risk of insulin over administration. In some embodiments, the basal rate profile optimizer provides upper and lower limits for the real-time basal rate adjustment, which may be defined as multiples of the pre-existing or pre-programmed basal rate, e.g. fractional values of less than 1 and greater than or equal to 0 to reduce insulin infusion in response to measured or predicted hypoglycemia and fractional values greater than 1 and less than or equal to 2 to increase insulin infusion in response to measured or predicted hyperglycemia.

For illustrative purposes, reference will now be made to FIG. 1, which is an exemplary environment in which some embodiments described herein may be implemented. Here, an analyte monitoring system 100 includes a continuous analyte sensor system 8. Continuous analyte sensor system 8 includes a sensor electronics module 12 and a continuous analyte sensor 10. The system 100 can also include other devices and/or sensors, such as a medicament delivery pump 2 and a reference analyte meter 4, as illustrated in FIG. 1. The continuous analyte sensor 10 may be physically connected to sensor electronics module 12 and may be integral with (e.g., non-releasably attached to) or releasably attachable to the continuous analyte sensor 10. Alternatively, the continuous analyte sensor 10 may be physically separate to sensor electronics module 12, but electronically coupled via inductive coupling or the like. Further, the sensor electronics module 12, medicament delivery pump 2, and/or analyte reference meter 4 may communicate with one or more additional devices, such as any or all of display devices 14, 16, 18 and 20.

The system 100 of FIG. 1 also includes a cloud-based processor 22 configured to analyze analyte data, medicament delivery data and/or other patient related data provided over network 24 directly or indirectly from one or more of sensor system 8, medicament delivery pump 2, reference analyte meter 4, and display devices 14, 16, 18, 20. Based on the received data, the processor 22 can further process the data, generate reports providing statistic based on the processed data, trigger notifications to electronic devices associated with the host or caretaker of the host, or provide processed information to any of the other devices of FIG. 1. In some exemplary implementations, the cloud-based processor 22 comprises one or more servers. If the cloud-based processor 22 comprises multiple servers, the servers can be either geographically local or separate from one another. The network 24 can include any wired and wireless communication medium to transmit data, including WiFi networks, cellular networks, the Internet and any combinations thereof.

It should be understood that although the example implementation described with respect to FIG. 1 refers to analyte data being received by processor 22, other types of data processed and raw data may be received as well.

In some exemplary implementations, the sensor electronics module 12 may include electronic circuitry associated with measuring and processing data generated by the continuous analyte sensor 10. This generated continuous analyte sensor data may also include algorithms, which can be used to process and calibrate the continuous analyte sensor data, although these algorithms may be provided in other ways as well. The sensor electronics module 12 may include hardware, firmware, software, or a combination thereof to provide measurement of levels of the analyte via a continuous analyte sensor, such as a continuous glucose sensor.

The sensor electronics module 12 may, as noted, couple (e.g., wirelessly and the like) with one or more devices, such as any or all of display devices 14, 16, 18, and 20. The display devices 14, 16, 18, and/or 20 may be configured for processing and presenting information, such sensor information transmitted by the sensor electronics module 12 for display at the display device. The display devices 14, 16, 18, and 20 can also trigger alarms based on the analyte sensor data.

In FIG. 1, display device 14 is a key fob-like display device, display device 16 is a hand-held application-specific computing device 16 (e.g. the DexCom G4® Platinum receiver commercially available from DexCom, Inc.), display device 18 is a general purpose smart phone or tablet computing device 20 (e.g. an Apple® iPhone®, iPad®, or iPod Touch® commercially available from Apple, Inc.), and display device 20 is a computer workstation 20. In some exemplary implementations, the relatively small, key fob-like display device 14 may be a computing device embodied in a wrist watch, a belt, a necklace, a pendent, a piece of jewelry, an adhesive patch, a pager, a key fob, a plastic card (e.g., credit card), an identification (ID) card, and/or the like. This small display device 14 may include a relatively small display (e.g., smaller than the display device 18) and may be configured to display a limited set of displayable sensor information, such as a numerical value 26 and an arrow 28. In contrast, display devices 16, 18 and 20 can be larger display devices that can be capable of displaying a larger set of displayable information, such as a trend graph 30 depicted on the hand-held receiver 16 in addition to other information such as a numerical value and arrow.

It is understood that any other user equipment (e.g. computing devices) configured to at least present information (e.g., a medicament delivery information, discrete self-monitoring analyte readings, heart rate monitor, caloric intake monitor, and the like) can be used in addition or instead of those discussed with reference to FIG. 1.

In some exemplary implementations of FIG. 1, the continuous analyte sensor 10 comprises a sensor for detecting and/or measuring analytes, and the continuous analyte sensor 10 may be configured to continuously detect and/or measure analytes as a non-invasive device, a subcutaneous device, a transdermal device, and/or an intravascular device. In some exemplary implementations, the continuous analyte sensor 10 may analyze a plurality of intermittent blood samples, although other analytes may be used as well.

In some exemplary implementations of FIG. 1, the continuous analyte sensor 10 may comprise a glucose sensor configured to measure glucose in the blood using one or more measurement techniques, such as enzymatic, chemical, physical, electrochemical, spectrophotometric, polarimetric, calorimetric, iontophoretic, radiometric, immunochemical, and the like. In implementations in which the continuous analyte sensor 10 includes a glucose sensor, the glucose sensor may be comprise any device capable of measuring the concentration of glucose and may use a variety of techniques to measure glucose including invasive, minimally invasive, and non-invasive sensing techniques (e.g., fluorescent monitoring), to provide a data, such as a data stream, indicative of the concentration of glucose in a host. The data stream may be raw data signal, which is converted into a calibrated and/or filtered data stream used to provide a value of glucose to a host, such as a user, a patient, or a caretaker (e.g., a parent, a relative, a guardian, a teacher, a doctor, a nurse, or any other individual that has an interest in the wellbeing of the host). Moreover, the continuous analyte sensor 10 may be implanted as at least one of the following types of sensors: an implantable glucose sensor, a transcutaneous glucose sensor, implanted in a host vessel or extracorporeally, a subcutaneous sensor, a refillable subcutaneous sensor, an intravascular sensor.

In some implementations of FIG. 1, the continuous analyte sensor system 8 includes a DexCom G4® Platinum glucose sensor and transmitter commercially available from DexCom, Inc., for continuously monitoring a host's glucose levels.

Figure 2:
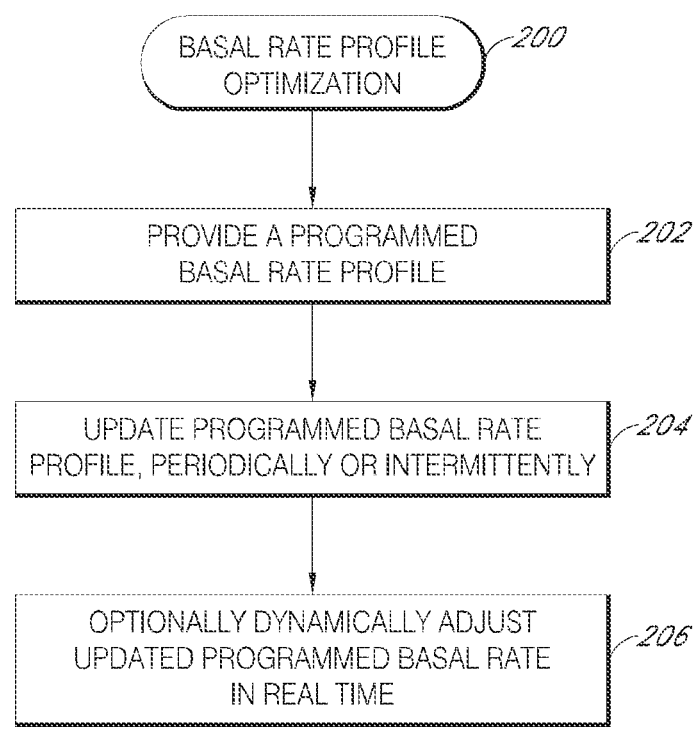
FIG. 2 is a flow chart that illustrates optimization of a basal rate profile in one embodiment.

FIG. 2 is a flow chart that illustrates optimization of a basal rate profile in accordance with some embodiments. Here, a processor module is configured to periodically optimize a basal rate profile using a time-averaged basal rate optimization performed over the previous about 3 to 7 days, which adjusts, or augments, the pre-programmed basal rate profile based thereon. The processor module can be embodied in any of the electronic devices described with reference to FIG. 1, such as the sensor system 8, medicament pump 2, reference meter 4, display device 14-20 and cloud-based processor 22. Further, the processor module need not be physically localized to a single electronic device, but can be separated between multiple devices. That is, the processor module can be physically divided between two more computing devices, such as sensor electronics 12 and medicament pump 2, or display device 16 and cloud-based processor 22.

In some embodiments, the retrospective time-averaged basal rate optimization utilizes sensor data from the continuous glucose sensor, for example, including periods of time spanning skipped meals per existing basal rate adjustment recommendations (see, e.g., Zisser H C, Bevier W C, Jovanovic L "Restoring euglycemia in the basal state using continuous glucose monitoring in subjects with type 1 diabetes mellitus" Diabetes Technol. Ther. 2007 December; 9(6):509-15) or, alternatively, from interpretation of meal data along with insulin data and the nutritional information for the meal. The output of the time-averaged basal rate optimization can be updated daily, weekly, or the like, to adjust the pre-programmed basal rate profile. In some implementations, a dynamic real-time basal rate optimizer operates to adjust the basal rate in real time within safety bounds determined by the optimized basal rate profile.

Basal rate profile optimization 200 is described in FIG. 2. At block 202 of FIG. 2, the processor module provides a programmed basal rate profile. For example, the pre-programmed basal rate profile can be programmed by a patient based on a consultation with a health care provider or by the patient alone. The basal rate may be selected from a list of predefined profiles provided by the manufacturer and/or manually defined by a user. In a feedback loop of the flowchart, the programmed basal rate profile at block 202 is an optimized basal rate profile from a previous update (at block 204), for example, from a previous day or week. The basal rate profile may consist of a single rate of insulin infusion over 24 hours or a plurality of rates associated with different time windows spanning a full 24 hours, as would be appreciated by one of ordinary skill in the art.

At block 204, the processor module updates the programmed basal rate profile of block 202, periodically or intermittently, based on a retrospective analysis of the continuous glucose sensor data (e.g., measured using sensor system 8 of FIG. 1) and optionally insulin data (e.g., generated by medicament delivery pump 2 of FIG. 1), if available, over a predetermined time window (e.g., about 3 to 7 days) for a particular patient. The updated basal rate profile may include a single basal rate profile for a particular patient, a profile defined by upper and lower limits (e.g., a range) for the maximum and minimum basal rates for a given patient and/or a combination of both.

The periodic or intermittent update can be performed once a day, triggered by an event or triggered based on a recognized pattern in the data, such as glycemic variability. A triggering event may be a failure of the real-time basal rate optimization to prevent a severe hypoglycemic episode (e.g., less than 55 mg/dL), a severe hyperglycemic episode (e.g., greater than 250 mg/dL) and/or a predefined pattern of severe hypoglycemic episodes or a severe hyperglycemic episode over the past window of time (e.g., 3-7 days). Pattern recognition algorithms that identify a predefined combination of frequency and severity of an event, such as described in such as described in co-pending patent application Ser. No. 13/566,678, filed 3 Aug. 2013 and Ser. No. 13/790,281, filed 8 Mar. 2013, may be useful as a triggering event. Additionally or alternatively, a predetermined pattern or repetition of hypoglycemia or hyperglycemia at certain times of day might trigger an update to the basal rate profile, including, for example, a decrease or increase in the pre-programmed basal rates at certain time blocks associated with the certain time of an identified pattern of hypo- or hyper-glycemia. Additional measures of glycemic variability, which may be used to trigger the update, have been described by Marling C R, Struble N W, Bunescu R C, Shubrook J H and Schwartz F L "A consensus perceived glycemic variability metric" *J Diabetes Sci Technol* 2013; 7(4):871-879.

The time-averaged basal rate optimization utilizes data over a moving window of previous days to determine an optimized basal rate profile which then provides input for and/or optionally safety bounds for the real-time basal rate adjustment and/or other closed loop control algorithm (at block 206). While not wishing to be bound by theory, the use of time averaging helps to reduce the effect of single day anomalies on the setting of the pre-programmed basal rates. The time-averaged basal rate optimization can be based on: continuous glucose sensor data, insulin delivery data, content of meals and/or physical activity during the period over which the time-averaging is being performed. The predetermined time window can be one day, 3 to 7 days, or longer. In some embodiments, the time window can be limited to reduce the effect of actual long-term changes in behavior or physical activity levels, for example, no more than 7, 14, 21 or 30 days. By periodically updating the basal rate profile based on a retrospective analysis of an immediately preceding time window of data, the updated programmed basal rate profile matches (e.g., more closely correlates) the patients' daily insulin dosing requirements as compared to the previous programmed basal rate profile. The matching or correlation of the basal rate profile with the patients' daily insulin dosing requirement can be quantified a measure of glycemic variability (e.g., time in/out target/euglycemia), especially in the absence of meals or other inputs that affect glycemic levels. The time averaged basal rate optimization can be performed locally on analyte sensor system 8, one of the display devices 14-20, medicament delivery pump 2, cloud-based processor 22, or the like.

In some embodiments detects sub-optimal basal rate profiles, and suggests improvements (to the patient, provider, or both). For example, prior to the processor module updating the programmed basal rate profile, the processor module may provide output indicative of a suboptimal basal rate profile, which may be detected based on a predetermined difference between the predetermined basal rate profile and the updated basal rate profile. The processor module may then output a message to a patient (e.g., via a prompt on a user interface) or to a care provider (e.g., via a message delivered wirelessly or via the internet) recommending the updated basal rate profile. The patient or care provider may then select or adjust the updated programmable basal rate profile, after which the processor module implements the updated basal rate profile on the medicament pump 2.

While personalized updating of the basal rate profile as described at block 204 is advantageous for use in optimizing stand-alone insulin pump therapy, the updated basal rate profile may also be used in closed loop or semi-closed loop system to improve the efficacy of closed loop algorithms. Namely, further improvements in semi-closed or closed loop algorithms may be achieved, over systems that use real time basal rate adjustments without utilizing the personalized basal rate profiles updates, by minimizing the required adjustment by the real-time basal rate adjustment due to the already personalized basal rate profile, which is described in more detail at block 206.

At block 206, the processor module dynamically adjusts (or augments), in real time, (e.g., increases or decreases) the basal rate of the updated programmed basal rate profile of block 204 in response to real time sensor data indicating actual or impending hyperglycemia or hypoglycemia. The indication of actual or impending hypoglycemia may be determined by comparing threshold criteria with estimated real time or predicted glucose concentration values, for example. The real-time adjustment of block 206 may be performed more often than the updating of the programmed basal rate profile of block 204 and generally utilizes a shorter time window of data and/or prediction of future glucose values and/or insulin-on-board information, for example, as compared to the time window of data used for the retrospective analysis of block 204. While not wishing to be bound by theory, the clinical effectiveness of a real-time basal rate dynamic adjust (or other closed loop control algorithm) of block 206 in providing incremental increases or decreases in basal insulin infusion in response to the real time sensor data is enhanced by utilizing an optimized programmed basal rate profile of block 204 as a starting point for insulin delivery.

Additionally or alternatively, retrospective analysis of continuous glucose monitoring data as part of the real-time basal rate adjustment and/or other closed loop control algorithm (at block 204) can provide upper and lower limits for the maximum and minimum basal rates for a given patient. For example, the upper and lower limits, defined by upper and lower basal rate profiles determined at block 204, may be applied to basal rates and/or other closed loop control algorithm. While not wishing to be bound by theory, it is believed that if the pre-programmed basal rate is not well correlated with the patient's daily insulin dosing requirements (as provided at block 204), then the safety constraints on the real-time basal rate adjustment or other closed loop control algorithm (at block 206) may limit the method and system from achieving good outcomes.

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The various operations of methods described above may be performed by any suitable means capable of performing the operations, such as various hardware and/or software component(s), circuits, and/or module(s). Generally, any operations illustrated in the Figures may be performed by corresponding functional means capable of performing the operations.

The various illustrative logical blocks, modules and circuits described in connection with the present disclosure (such as the blocks of FIG. 2) may be implemented or performed with a general purpose processor, a digital signal processor (DSP), an application specific integrated circuit (ASIC), a field programmable gate array signal (FPGA) or other programmable logic device (PLD), discrete gate or transistor logic, discrete hardware components or any combination thereof designed to perform the functions described herein. A general purpose processor may be a microprocessor, but in the alternative, the processor may be any commercially available processor, controller, microcontroller or state machine. A processor may also be implemented as a combination of computing devices, e.g., a combination of a DSP and a microprocessor, a plurality of microprocessors, one or more microprocessors in conjunction with a DSP core, or any other such configuration.

In one or more aspects, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Thus, in some aspects computer readable medium may comprise non-transitory computer readable medium (e.g., tangible media). In addition, in some aspects computer readable medium may comprise transitory computer readable medium (e.g., a signal). Combinations of the above should also be included within the scope of computer-readable media.

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

Thus, certain aspects may comprise a computer program product for performing the operations presented herein. For example, such a computer program product may comprise a computer readable medium having instructions stored (and/or encoded) thereon, the instructions being executable by one or more processors to perform the operations described herein. For certain aspects, the computer program product may include packaging material.

Software or instructions may also be transmitted over a transmission medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of transmission medium.

Further, it should be appreciated that modules and/or other appropriate means for performing the methods and techniques described herein can be downloaded and/or otherwise obtained by a user terminal and/or base station as applicable. For example, such a device can be coupled to a server to facilitate the transfer of means for performing the methods described herein. Alternatively, various methods described herein can be provided via storage means (e.g., RAM, ROM, a physical storage medium such as a compact disc (CD) or floppy disk, etc.), such that a user terminal and/or base station can obtain the various methods upon coupling or providing the storage means to the device. Moreover, any other suitable technique for providing the methods and techniques described herein to a device can be utilized.

It is to be understood that the claims are not limited to the precise configuration and components illustrated above. Various modifications, changes and variations may be made in the arrangement, operation and details of the methods and apparatus described above without departing from the scope of the claims.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated. Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction 'and' should not be read as requiring that each and every one of those items be present in the grouping, but rather should be read as 'and/or' unless expressly stated otherwise. Similarly, a group of items linked with the conjunction 'or' should not be read as requiring mutual exclusivity among that group, but rather should be read as 'and/or' unless expressly stated otherwise.

Where a range of values is provided, it is understood that the upper and lower limit, and each intervening value between the upper and lower limit of the range is encompassed within the embodiments.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention, e.g., as including any combination of the listed items, including single members (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

All references cited herein are incorporated herein by reference in their entirety. To the extent publications and patents or patent applications incorporated by reference contradict the disclosure contained in the specification, the specification is intended to supersede and/or take precedence over any such contradictory material.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method for optimizing a basal rate profile for use with continuous insulin therapy, comprising:
    providing a determined basal rate profile from a control algorithm for insulin therapy, wherein the determined basal rate profile comprises an insulin delivery schedule that includes one or more blocks of time, wherein each of the one or more blocks of time defines a basal insulin delivery rate, and wherein each basal insulin delivery rate is determined from the control algorithm;
    periodically or intermittently updating the determined basal rate profile based on a retrospective analysis of continuous glucose sensor data, insulin delivery data, or both, over a moving window of time that precedes the periodic or intermittent update of the determined basal rate profile, wherein the moving window of time comprises:
        a first time window preceding a first periodic or intermittent update, and
        a second time window preceding a second periodic or intermittent update,
        wherein the second time window ends later than the first time window; and
    dynamically adjusting a basal insulin delivery rate of the determined basal rate profile in response to continuous glucose sensor data,
    wherein dynamically adjusting the basal insulin delivery rate comprises incrementally increasing or decreasing basal insulin delivery in response to real time continuous glucose sensor data indicating impending hyperglycemia or impending hypoglycemia.

2. The method of claim 1, wherein the basal insulin delivery rate consists of a continuous delivery of baseline insulin throughout a 24-hour period.

3. The method of claim 1, wherein the determined basal rate profile consists of a constant basal insulin delivery rate throughout a 24-hour period.

4. The method of claim 1, wherein the dynamically adjusting the basal insulin delivery rate in response to real time continuous glucose sensor data is performed by a second control algorithm different from the control algorithm that determines the determined basal rate profile.

5. The method of claim 1, wherein the basal insulin delivery rate, the insulin delivery rate dynamically adjusted relative to the basal insulin delivery rate, or both are constrained by a maximum limit.

6. The method of claim 5, wherein the maximum limit is determined by a control algorithm.

7. The method of claim 1, wherein the periodically or intermittently updating the determined basal rate profile uses a closed loop algorithm triggered by an event.

8. The method of claim 1, further comprising iteratively repeating the periodically or intermittently updating the determined basal rate profile, wherein the determined basal rate profile for a current iteration is an updated basal rate profile from a previous iteration.

9. The method of claim 8, wherein the previous iteration is from about one day to one week previous to the current iteration.

10. The method of claim 1, wherein the periodically or intermittently updating the determined basal rate profile is based at least in part on a retrospective analysis of insulin delivery data.

11. The method of claim 10, wherein the retrospective analysis comprises a time-averaging of the insulin delivery data.

12. The method of claim 1, wherein dynamically adjusting the basal insulin delivery rate comprises augmenting the basal insulin delivery rate.

13. The method of claim 1, wherein dynamically adjusting the basal insulin delivery rate comprises multiplying the basal insulin delivery rate by a fractional value of less than or greater than 1.

14. The method of claim 1, wherein the retrospective analysis is performed over a moving window of time that is 3 to 30 days in duration, and wherein the first time window and the second time window are of the same duration or different durations.

15. A non-transitory computer-readable medium, comprising instructions for causing a computing device to perform a method, the method comprising:
providing a determined basal rate profile from a control algorithm for insulin therapy, wherein the determined basal rate profile comprises an insulin delivery schedule that includes one or more blocks of time, wherein each of the one or more blocks of time defines a basal insulin delivery rate, and wherein each basal insulin delivery rate is determined from the control algorithm;
periodically or intermittently updating the determined basal rate profile based on a retrospective analysis of continuous glucose sensor data, insulin delivery data, or both, over a moving window of time that precedes the periodic or intermittent update of the determined basal rate profile, wherein the moving window of time comprises:
a first time window preceding a first periodic or intermittent update, and
a second time window preceding a second periodic or intermittent update,
wherein the second time window ends later than the first time window; and
dynamically adjusting a basal insulin delivery rate of the determined basal rate profile in response to real time continuous glucose sensor data,
wherein dynamically adjusting a basal insulin delivery rate comprises increasing or decreasing insulin delivery relative to a basal insulin delivery rate of the determined basal rate profile in response to real time continuous glucose sensor data indicating impending hyperglycemia or impending hypoglycemia.

16. The non-transitory computer-readable medium of claim 15, wherein the computing device is integrated with an insulin delivery pump.

17. A system including a medicament delivery pump and a processor configured to deliver a medicament to a host, comprising:
a processor module configured to:
provide a determined basal rate profile from a control algorithm for insulin therapy, wherein the determined basal rate profile comprises an insulin delivery schedule that includes one or more blocks of time, wherein each of the one or more blocks of time defines a basal insulin delivery rate, and wherein each basal insulin delivery rate is determined from the control algorithm;
periodically or intermittently update the determined basal rate profile based on a retrospective analysis of continuous glucose sensor data, insulin delivery data, or both, over a moving window of time that precedes the periodic or intermittent update of the determined basal rate profile, wherein the moving window of time comprises:
a first time window preceding a first periodic or intermittent update, and
a second time window preceding a second periodic or intermittent update,
wherein the second time window ends later than the first time window; and
dynamically adjust a basal insulin delivery rate of the determined basal rate profile in response to real time continuous glucose sensor data,
wherein dynamically adjusting a basal insulin delivery rate comprises using a predictive algorithm to increase or decrease insulin delivery relative to a basal insulin delivery rate of the determined basal rate profile in response to real time continuous glucose sensor data indicating actual hyperglycemia, impending hyperglycemia, actual hypoglycemia, or impending hypoglycemia.

18. The system of claim 17, wherein the basal insulin delivery rate consists of a continuous delivery of baseline insulin throughout a 24-hour period.

19. The system of claim 17, wherein the determined basal rate profile consists of a constant basal insulin delivery rate throughout a 24-hour period.

20. The system of claim 17, wherein the system is configured to dynamically adjust the basal insulin delivery rate in response to real time continuous glucose sensor data with a second control algorithm different from the control algorithm that determines the determined basal rate profile.

21. The system of claim 17, wherein the basal insulin delivery rate, the dynamically adjusted basal insulin delivery rate, or both are constrained by a maximum limit.

22. The system of claim 21, wherein the maximum limit is determined by a control algorithm.

23. The system of claim 17, wherein the processor module is configured to trigger the periodically or intermittently updating of the determined basal rate profile based on an event.

24. The system of claim 17, wherein the determined basal rate profile for a current iteration is an updated basal rate profile from a previous iteration.

25. The system of claim 24, wherein the previous iteration is from about one day to one week previous to the current iteration.

26. The system of claim 17, wherein the periodically or intermittently updating the determined basal rate profile is based at least in part on a retrospective analysis of insulin delivery data.

27. The system of claim 26, wherein the retrospective analysis comprises a time-averaging of the insulin delivery data.

28. The system of claim 17, wherein dynamically adjusting the basal insulin delivery rate comprises augmenting the basal insulin delivery rate for one or more blocks of time.

29. The system of claim 17, wherein dynamically adjusting the basal insulin delivery rate comprises multiplying the basal insulin delivery rate by a fractional value of less than or greater than 1.

30. The system of claim 17, wherein the retrospective analysis is performed over a moving window of time that is 3 to 30 days in duration, and wherein the first time window and the second time window are of the same duration or different durations.

\* \* \* \* \*